(12) United States Patent
Mouchawar et al.

(10) Patent No.: US 6,738,668 B1
(45) Date of Patent: May 18, 2004

(54) IMPLANTABLE CARDIAC STIMULATION DEVICE HAVING A CAPTURE ASSURANCE SYSTEM WHICH MINIMIZES BATTERY CURRENT DRAIN AND METHOD FOR OPERATING THE SAME

(75) Inventors: Nabil A. Mouchawar, Newhall, CA (US); Gabriel A. Mouchawar, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 73 days.

(21) Appl. No.: 10/000,058

(22) Filed: Nov. 1, 2001

(51) Int. Cl.$^7$ ................................................ A61N 1/37
(52) U.S. Cl. ...................................................... 607/28
(58) Field of Search ....................................... 607/5–28

(56) References Cited

U.S. PATENT DOCUMENTS

| | | | |
|---|---|---|---|
| 4,712,555 A | 12/1987 | Thornander et al. | 128/419 PG |
| 4,788,980 A | 12/1988 | Mann et al. | 128/419 PG |
| 4,809,697 A | 3/1989 | Causey, III et al. | 128/419 PT |
| 4,940,052 A | 7/1990 | Mann et al. | 128/419 PG |
| 4,944,298 A | 7/1990 | Sholder | 128/419 PG |
| 4,944,299 A | 7/1990 | Silvian | 128/419 PG |
| 5,320,643 A | * 6/1994 | Roline et al. | |
| 5,350,410 A | 9/1994 | Kleks et al. | 607/28 |
| 5,447,525 A | 9/1995 | Powell et al. | 607/28 |
| 5,480,414 A | * 1/1996 | Stroebel et al. | |
| 5,669,392 A | 9/1997 | Ljungström | 128/704 |
| 5,697,956 A | 12/1997 | Bornzin | 607/28 |
| 5,782,889 A | 7/1998 | Högnelid et al. | 607/28 |
| 5,846,264 A | 12/1998 | Andersson et al. | 607/28 |

OTHER PUBLICATIONS

Stokes, Ken, et al., The Electrode–Biointerface: Stimulation, Modern Cardiac Pacing, Chapter 3, pp: 33–77 (1985).

* cited by examiner

*Primary Examiner*—Scott M. Getzow

(57) ABSTRACT

An improved pacing system and related method for use in an implantable pacemaker or defibrillator are disclosed which operate using a predetermined subset of combinations of possible combinations for pacing stimulus pulse amplitude and pulse width, which subset of combinations are the most energy-efficient pairs, thereby ensuring reduced battery current drain. This is accomplished by ensuring that each combination has the lowest battery charge drain of any combination having at least the rheobase value of that particular combination as a function of cardiac chronaxie. The preferred embodiment of the pacing system of the present invention includes capture verification to enable a substantially reduced safety margin to further minimize the level of battery charge drain. The preferred embodiment of the pacing system of the present invention also includes the capability to produce a safety backup pulse, to ensure that the pacing system never misses a beat. The preferred embodiment of the pacing system of the present invention further includes the capability to initially and periodically determine the stimulation threshold and cardiac chronaxie.

28 Claims, 10 Drawing Sheets

FIG. 3

| | PULSE WIDTH (PW) | | | | | | | |
|---|---|---|---|---|---|---|---|---|
| | 0.2 | 0.4 | 0.6 | 0.8 | 1 | 1.2 | 1.4 | 1.6 |
| 0.5 | 0.20 | 0.40 | 0.60 | 0.80 | 1.00 | 1.20 | 1.40 | 1.60 |
| 0.75 | 0.30 | 0.60 | 0.90 | 1.20 | 1.50 | 1.80 | 2.10 | 2.40 |
| 1 | 0.40 | 0.80 | 1.20 | 1.60 | 2.00 | 2.40 | 2.80 | 3.20 |
| 1.25 | 0.50 | 1.00 | 1.50 | 2.00 | 2.50 | 3.00 | 3.50 | 4.00 |
| 1.5 | 0.60 | 1.20 | 1.80 | 2.40 | 3.00 | 3.60 | 4.20 | 4.80 |
| 1.75 | 0.70 | 1.40 | 2.10 | 2.80 | 3.50 | 4.20 | 4.90 | 5.60 |
| 2 | 0.80 | 1.60 | 2.40 | 3.20 | 4.00 | 4.80 | 5.60 | 6.40 |
| 2.25 | 0.90 | 1.80 | 2.70 | 3.60 | 4.50 | 5.40 | 6.30 | 7.20 |
| 2.5 | 1.00 | 2.00 | 3.00 | 4.00 | 5.00 | 6.00 | 7.00 | 8.00 |
| 2.75 | 2.20 | 4.40 | 6.60 | 8.80 | 11.00 | 13.20 | 15.40 | 17.60 |
| 3 | 2.40 | 4.80 | 7.20 | 9.60 | 12.00 | 14.40 | 16.80 | 19.20 |
| 3.25 | 2.60 | 5.20 | 7.80 | 10.40 | 13.00 | 15.60 | 18.20 | 20.80 |
| 3.5 | 2.80 | 5.60 | 8.40 | 11.20 | 14.00 | 16.80 | 19.60 | 22.40 |
| 3.75 | 3.00 | 6.00 | 9.00 | 12.00 | 15.00 | 18.00 | 21.00 | 24.00 |
| 4 | 3.20 | 6.40 | 9.60 | 12.80 | 16.00 | 19.20 | 22.40 | 25.60 |
| 4.25 | 3.40 | 6.80 | 10.20 | 13.60 | 17.00 | 20.40 | 23.80 | 27.20 |
| 4.5 | 3.60 | 7.20 | 10.80 | 14.40 | 18.00 | 21.60 | 25.20 | 28.80 |
| 4.75 | 3.80 | 7.60 | 11.40 | 15.20 | 19.00 | 22.80 | 26.60 | 30.40 |
| 5 | 4.00 | 8.00 | 12.00 | 16.00 | 20.00 | 24.00 | 28.00 | 32.00 |
| 5.25 | 6.30 | 12.60 | 18.90 | 25.20 | 31.50 | 37.80 | 44.10 | 50.40 |
| 5.5 | 6.60 | 13.20 | 19.80 | 26.40 | 33.00 | 39.60 | 46.20 | 52.80 |
| 5.75 | 6.90 | 13.80 | 20.70 | 27.60 | 34.50 | 41.40 | 48.30 | 55.20 |
| 6 | 7.20 | 14.40 | 21.60 | 28.80 | 36.00 | 43.20 | 50.40 | 57.60 |
| 6.25 | 7.50 | 15.00 | 22.50 | 30.00 | 37.50 | 45.00 | 52.50 | 60.00 |
| 6.5 | 7.80 | 15.60 | 23.40 | 31.20 | 39.00 | 46.80 | 54.60 | 62.40 |
| 6.75 | 8.10 | 16.20 | 24.30 | 32.40 | 40.50 | 48.60 | 56.70 | 64.80 |
| 7 | 8.40 | 16.80 | 25.20 | 33.60 | 42.00 | 50.40 | 58.80 | 67.20 |
| 7.25 | 8.70 | 17.40 | 26.10 | 34.80 | 43.50 | 52.20 | 60.90 | 69.60 |
| 7.5 | 9.00 | 18.00 | 27.00 | 36.00 | 45.00 | 54.00 | 63.00 | 72.00 |

Row labels (left axis): PULSE AMPLITUDE (PA)

TABLE VALUES=CHARGE FROM BATTERY

FIG. 4 c=0.4ms

| | | PULSE WIDTH (PW) | | | | | | | |
|---|---|---|---|---|---|---|---|---|---|
| | | 0.2 | 0.4 | 0.6 | 0.8 | 1 | 1.2 | 1.4 | 1.6 |
| PULSE AMPLITUDE (PA) | 0.5 | 0.17 | 0.25 | 0.30 | 0.33 | 0.36 | 0.38 | 0.39 | 0.40 |
| | 0.75 | 0.25 | 0.38 | 0.45 | 0.50 | 0.54 | 0.56 | 0.58 | 0.60 |
| | 1 | 0.33 | 0.50 | 0.60 | 0.67 | 0.71 | 0.75 | 0.78 | 0.80 |
| | 1.25 | 0.42 | 0.63 | 0.75 | 0.83 | 0.89 | 0.94 | 0.97 | 1.00 |
| | 1.5 | 0.50 | 0.75 | 0.90 | 1.00 | 1.07 | 1.13 | 1.17 | 1.20 |
| | 1.75 | 0.58 | 0.88 | 1.05 | 1.17 | 1.25 | 1.31 | 1.36 | 1.40 |
| | 2 | 0.67 | 1.00 | 1.20 | 1.33 | 1.43 | 1.50 | 1.56 | 1.60 |
| | 2.25 | 0.75 | 1.13 | 1.35 | 1.50 | 1.61 | 1.69 | 1.75 | 1.80 |
| | 2.5 | 0.83 | 1.25 | 1.50 | 1.67 | 1.79 | 1.88 | 1.94 | 2.00 |
| | 2.75 | 0.92 | 1.38 | 1.65 | 1.83 | 1.96 | 2.06 | 2.14 | 2.20 |
| | 3 | 1.00 | 1.50 | 1.80 | 2.00 | 2.14 | 2.25 | 2.33 | 2.40 |
| | 3.25 | 1.08 | 1.63 | 1.95 | 2.17 | 2.32 | 2.44 | 2.53 | 2.60 |
| | 3.5 | 1.17 | 1.75 | 2.10 | 2.33 | 2.50 | 2.63 | 2.72 | 2.80 |
| | 3.75 | 1.25 | 1.88 | 2.25 | 2.50 | 2.68 | 2.81 | 2.92 | 3.00 |
| | 4 | 1.33 | 2.00 | 2.40 | 2.67 | 2.86 | 3.00 | 3.11 | 3.20 |
| | 4.25 | 1.42 | 2.13 | 2.55 | 2.83 | 3.04 | 3.19 | 3.31 | 3.40 |
| | 4.5 | 1.50 | 2.25 | 2.70 | 3.00 | 3.21 | 3.38 | 3.50 | 3.60 |
| | 4.75 | 1.58 | 2.38 | 2.85 | 3.17 | 3.39 | 3.56 | 3.69 | 3.80 |
| | 5 | 1.67 | 2.50 | 3.00 | 3.33 | 3.57 | 3.75 | 3.89 | 4.00 |
| | 5.25 | 1.75 | 2.63 | 3.15 | 3.50 | 3.75 | 3.94 | 4.08 | 4.20 |
| | 5.5 | 1.83 | 2.75 | 3.30 | 3.67 | 3.93 | 4.13 | 4.28 | 4.40 |
| | 5.75 | 1.92 | 2.88 | 3.45 | 3.83 | 4.11 | 4.31 | 4.47 | 4.60 |
| | 6 | 2.00 | 3.00 | 3.60 | 4.00 | 4.29 | 4.50 | 4.67 | 4.80 |
| | 6.25 | 2.08 | 3.13 | 3.75 | 4.17 | 4.46 | 4.69 | 4.86 | 5.00 |
| | 6.5 | 2.17 | 3.25 | 3.90 | 4.33 | 4.64 | 4.88 | 5.06 | 5.20 |
| | 6.75 | 2.25 | 3.38 | 4.05 | 4.50 | 4.82 | 5.06 | 5.25 | 5.40 |
| | 7 | 2.33 | 3.50 | 4.20 | 4.67 | 5.00 | 5.25 | 5.44 | 5.60 |
| | 7.25 | 2.42 | 3.63 | 4.35 | 4.83 | 5.18 | 5.44 | 5.64 | 5.80 |
| | 7.5 | 2.50 | 3.75 | 4.50 | 5.00 | 5.36 | 5.63 | 5.83 | 6.00 |

TABLE VALUES=RHEOBASE c=0.2ms

| | PULSE WIDTH (PW) | | | | | | | |
|---|---|---|---|---|---|---|---|---|
| | | 0.2 | 0.4 | 0.6 | 0.8 | 1 | 1.2 | 1.4 | 1.6 |
| PULSE AMPLITUDE (PA) | 0.5 | 0.25 | 0.33 | 0.38 | 0.40 | 0.42 | 0.43 | 0.44 | 0.44 |
| | 0.75 | 0.38 | 0.50 | 0.56 | 0.60 | 0.63 | 0.64 | 0.66 | 0.67 |
| | 1 | 0.50 | 0.67 | 0.75 | 0.80 | 0.83 | 0.86 | 0.88 | 0.89 |
| | 1.25 | 0.63 | 0.83 | 0.94 | 1.00 | 1.04 | 1.07 | 1.09 | 1.11 |
| | 1.5 | 0.75 | 1.00 | 1.13 | 1.20 | 1.25 | 1.29 | 1.31 | 1.33 |
| | 1.75 | 0.88 | 1.17 | 1.31 | 1.40 | 1.46 | 1.50 | 1.53 | 1.56 |
| | 2 | 1.00 | 1.33 | 1.50 | 1.60 | 1.67 | 1.71 | 1.75 | 1.78 |
| | 2.25 | 1.13 | 1.50 | 1.69 | 1.80 | 1.88 | 1.93 | 1.97 | 2.00 |
| | 2.5 | 1.25 | 1.67 | 1.88 | 2.00 | 2.08 | 2.14 | 2.19 | 2.22 |
| | 2.75 | 1.38 | 1.83 | 2.06 | 2.20 | 2.29 | 2.36 | 2.41 | 2.44 |
| | 3 | 1.50 | 2.00 | 2.25 | 2.40 | 2.50 | 2.57 | 2.63 | 2.67 |
| | 3.25 | 1.63 | 2.17 | 2.44 | 2.60 | 2.71 | 2.79 | 2.84 | 2.89 |
| | 3.5 | 1.75 | 2.33 | 2.63 | 2.80 | 2.92 | 3.00 | 3.06 | 3.11 |
| | 3.75 | 1.88 | 2.50 | 2.81 | 3.00 | 3.13 | 3.21 | 3.28 | 3.33 |
| | 4 | 2.00 | 2.67 | 3.00 | 3.20 | 3.33 | 3.43 | 3.50 | 3.56 |
| | 4.25 | 2.13 | 2.83 | 3.19 | 3.40 | 3.54 | 3.64 | 3.72 | 3.78 |
| | 4.5 | 2.25 | 3.00 | 3.38 | 3.60 | 3.75 | 3.86 | 3.94 | 4.00 |
| | 4.75 | 2.38 | 3.17 | 3.56 | 3.80 | 3.96 | 4.07 | 4.16 | 4.22 |
| | 5 | 2.50 | 3.33 | 3.75 | 4.00 | 4.17 | 4.29 | 4.38 | 4.44 |

TABLE VALUES=RHEOBASE

FIG. 5 c=0.6ms

| PULSE WIDTH (PW) | | | | | | | | |
|---|---|---|---|---|---|---|---|---|
| | | 0.2 | 0.4 | 0.6 | 0.8 | 1 | 1.2 | 1.4 | 1.6 |
| PULSE AMPLITUDE (PA) | 0.5 | 0.13 | 0.20 | 0.25 | 0.29 | 0.31 | 0.33 | 0.35 | 0.36 |
| | 0.75 | 0.19 | 0.30 | 0.38 | 0.43 | 0.47 | 0.50 | 0.53 | 0.55 |
| | 1 | 0.25 | 0.40 | 0.50 | 0.57 | 0.63 | 0.67 | 0.70 | 0.73 |
| | 1.25 | 0.31 | 0.50 | 0.63 | 0.71 | 0.78 | 0.83 | 0.88 | 0.91 |
| | 1.5 | 0.38 | 0.60 | 0.75 | 0.86 | 0.94 | 1.00 | 1.05 | 1.09 |
| | 1.75 | 0.44 | 0.70 | 0.88 | 1.00 | 1.09 | 1.17 | 1.23 | 1.27 |
| | 2 | 0.50 | 0.80 | 1.00 | 1.14 | 1.25 | 1.33 | 1.40 | 1.45 |
| | 2.25 | 0.56 | 0.90 | 1.13 | 1.29 | 1.41 | 1.50 | 1.58 | 1.64 |
| | 2.5 | 0.63 | 1.00 | 1.25 | 1.43 | 1.56 | 1.67 | 1.75 | 1.82 |
| | 2.75 | 0.69 | 1.10 | 1.38 | 1.57 | 1.72 | 1.83 | 1.93 | 2.00 |
| | 3 | 0.75 | 1.20 | 1.50 | 1.71 | 1.88 | 2.00 | 2.10 | 2.18 |
| | 3.25 | 0.81 | 1.30 | 1.63 | 1.86 | 2.03 | 2.17 | 2.28 | 2.36 |
| | 3.5 | 0.88 | 1.40 | 1.75 | 2.00 | 2.19 | 2.33 | 2.45 | 2.55 |
| | 3.75 | 0.94 | 1.50 | 1.88 | 2.14 | 2.34 | 2.50 | 2.63 | 2.73 |
| | 4 | 1.00 | 1.60 | 2.00 | 2.29 | 2.50 | 2.67 | 2.80 | 2.91 |
| | 4.25 | 1.06 | 1.70 | 2.13 | 2.43 | 2.66 | 2.83 | 2.98 | 3.09 |
| | 4.5 | 1.13 | 1.80 | 2.25 | 2.57 | 2.81 | 3.00 | 3.15 | 3.27 |
| | 4.75 | 1.19 | 1.90 | 2.38 | 2.71 | 2.97 | 3.17 | 3.33 | 3.45 |
| | 5 | 1.25 | 2.00 | 2.50 | 2.86 | 3.13 | 3.33 | 3.50 | 3.64 |

TABLE VALUES=RHEOBASE

FIG. 6

| *PA | *PW | Vb | Q |
|---|---|---|---|
| 0.50 | 0.20 | 0.17 | 0.20 |
| 0.75 | 0.20 | 0.25 | 0.30 |
| 1.00 | 0.20 | 0.33 | 0.40 |
| 1.25 | 0.20 | 0.42 | 0.50 |
| 1.50 | 0.20 | 0.50 | 0.60 |
| 1.75 | 0.20 | 0.58 | 0.70 |
| 2.00 | 0.20 | 0.67 | 0.80 |
| 2.25 | 0.20 | 0.75 | 0.90 |
| 2.50 | 0.20 | 0.83 | 1.00 |
| 1.75 | 0.40 | 0.88 | 0.50 |
| 2.00 | 0.40 | 1.00 | 0.57 |
| 2.25 | 0.40 | 1.13 | 0.64 |
| 2.50 | 0.40 | 1.25 | 0.71 |
| 2.25 | 0.60 | 1.35 | 2.70 |
| 2.50 | 0.60 | 1.50 | 3.00 |
| 2.50 | 0.80 | 1.67 | 4.00 |
| 2.50 | 1.00 | 1.79 | 5.00 |
| 2.50 | 1.20 | 1.88 | 6.00 |
| 4.0 | 0.40 | 2.00 | 6.40 |
| 6.75 | 0.40 | 3.38 | 16.20 |
| 7.0 | 0.40 | 3.50 | 16.80 |
| 7.25 | 0.40 | 3.63 | 17.40 |
| 7.5 | 0.40 | 3.75 | 18.00 |
| 7 | 0.60 | 4.20 | 25.20 |
| 7.25 | 0.60 | 4.35 | 26.10 |
| 7.5 | 0.6 | 4.5 | 27.00 |
| 7.0 | 0.8 | 4.64 | 33.60 |
| 7.25 | 0.8 | 4.83 | 34.88 |
| 7.5 | 0.8 | 5.00 | 36.00 |
| 7.25 | 1.0 | 5.18 | 43.50 |
| 7.5 | 1.0 | 5.36 | 45.00 |
| 7.25 | 1.2 | 5.44 | 52.20 |
| 7.50 | 1.2 | 5.63 | 54.00 |
| 7.25 | 1.4 | 5.60 | 60.90 |
| 7.50 | 1.4 | 5.83 | 63.00 |
| 7.50 | 1.6 | 6.00 | 72.00 |

FIG. 7 c=0.4 ms

IMPLANTABLE CARDIAC STIMULATION DEVICE HAVING A CAPTURE ASSURANCE SYSTEM WHICH MINIMIZES BATTERY CURRENT DRAIN AND METHOD FOR OPERATING THE SAME

FIELD OF THE INVENTION

The present invention relates generally to implantable cardiac stimulation devices, and more particularly to an automatic pacing stimulus capture assurance system and related method for use in an implantable pacemaker or defibrillator.

BACKGROUND OF THE INVENTION

Pacemakers are used to treat a condition called bradycardia, in which the heart beats too slowly. A pacemaker system includes three components—a pulse generator, at least one pacing lead, and a programmer. The pulse generator contains the battery and the electronic circuitry, or "brain," which directs the pulse generator to send electrical stimulation pulses through the pacing leads, stimulating the heart and causing it to beat at a controlled "normal" rhythm. The pacing leads may also be used to transmit cardiac signals (i.e., depolarization signals) to the pulse generator. Pacemakers may also include physiological sensors which provide the pacemaker with an indicia of patient hemodynamic needs, so that the pacemaker can adjust its pacing strategy to satisfy those needs. An external programmer is used to monitor the operation of the pacemaker noninvasively (referred to as interrogating the pacemaker) and to change pacemaker settings (referred to as programming the pacemaker).

Implantable cardioverter/defibrillators (ICD's) are used to treat a condition called tachycardia, in which the heart beats at a rapid, uncoordinated manner. An ICD system, like a pacemaker system, is made up of three components—an ICD pulse generator, at least one lead, and a programmer used to interrogate and program the ICD. The ICD pulse generator monitors the rhythm of the heart from the leads, and administers an electric shock when necessary to control/terminate tachycardias and restore a normal heartbeat. ICD's also include pacemakers, since many patients needing an ICD can generally benefit from some pacing therapy.

Pacemaker technology has evolved rapidly over the last several decades, resulting in improvements making pacemakers more automatic in their ability to adapt to the specific needs of individual patients. ICD's have also evolved to become increasingly sophisticated both in their treatment of tachycardias and in their inclusion of full-featured pacemakers. In addition, both pacemakers and ICD's have become significantly smaller with greater longevity resulting from increasingly efficient operation which conserves battery power. It is certainly widely appreciated by those skilled in the art that it is imperative to minimize the operating current required by these devices to achieve the twin goals of extending their operating lives and making the device size as small as is possible.

One of the most significant ways of increasing the efficiency of pacemakers, as well as the pacemaker system operation in ICD's, has been the development of systems which automatically and continuously adjust the level of energy of electrical stimulation pulses delivered to pace the patient's heart. In order for a stimulation pulse from a pacemaker to depolarize cardiac muscle tissue to cause it to contract (to cause a heartbeat), the energy of the stimulation pulse must be sufficient to "capture" the heart, that is to cause a depolarization of the atrium or ventricle. The level of energy in a pacemaker stimulation pulse which is necessary to cause capture is referred to as the stimulation threshold level, or simply as the stimulation threshold. Most pacemakers and ICD's are capable of determining the stimulation threshold in a test which reduces stimulation pulse energy until loss of capture is detected.

If the stimulation pulse is below the stimulation threshold, capture will not occur and the stimulation pulse will be ineffective. If, on the other hand, the stimulation pulse is at or above the stimulation threshold, capture will most likely occur. The amount of energy in the pacemaker stimulation pulse above the stimulation threshold provides no useful function and is wasted. For the purposes of conserving battery energy, and maximizing the life of the device, it is desirable to keep the amount of energy in the pacemaker stimulation pulse or slightly above at the stimulation threshold.

The stimulation threshold varies widely, not only from patient to patient but for any given patient substantially over both longer and shorter periods of time. Eating and sleeping can cause about a twenty percent increase in the stimulation threshold. Posture and exercise can change the stimulation threshold about fifteen to twenty percent. Following lead implantation, the stimulation threshold typically increases to a peak level three months after implantation, and then stabilizes at a lower level.

Since it is desirable to ensure capture, physicians typically program the pacemaker or ICD to deliver pacemaker stimulation pulses at an energy level substantially above the stimulation threshold. The amount that the pacemaker stimulation pulse energy exceeds the stimulation threshold is referred to as the "safety factor." Physicians generally program the stimulation pulse energy at a safety factor of 1.7 to 2 times the stimulation threshold. It is well appreciated by those skilled in the art that the safety factor results in a substantially increased level of current drain from the battery, and in reduced device longevity. Since patient safety is paramount, this has been a situation which, until a few years ago, was acceptable.

Recently, the first pacemakers with automatic capture confirmation on a beat by beat basis were developed. They combine automatic backup pulse delivery upon loss of capture with automatic output regulation of stimulation pulse levels to a value just above the stimulation threshold. These devices automatically search for and locate the stimulation threshold and pace at a level just above that stimulation threshold (for example, 0.3 volts above the stimulation threshold), typically with the amplitude or voltage level of the stimulation pulse being varied and the pulse width remaining constant, such as, for example, at a nominal value of 0.5 mS. Such a stimulation threshold search may be automatically done periodically, such as, for example, every eight hours.

These devices also monitor capture confirmation by looking for an evoked response during a window of time immediately after the stimulation pulse; for example, the window may begin 15 mS after each stimulation pulse, with the width of the window being 47.5 mS. Finally, these devices assume loss of capture if no evoked response is sensed during the window after the stimulation pulse, and, in the absence of an evoked response signal, provide a higher voltage (typically 4.5 volts, for example) safety backup pulse. Thus, the device ensures that the patient's heart never misses a beat. In the event of loss of capture indicating a change in the stimulation threshold (which may be presumed, for example, after the delivery of two consecutive backup pulses), the device will search again for the stimulation threshold.

One example of a system for locating the stimulation threshold is shown in U.S. Pat. No. 5,669,392, to Ljungström. Similarly, an example of a capture confirmation system is illustrated in U.S. Pat. No. 5,782,889, to Höegnelid et al. Finally, an example of a system for automatically providing a backup pulse is shown in U.S. Pat. No. 5,846,264, to Andersson et al., all of which are each hereby incorporated herein by reference.

Another automatic system having similar characteristics is described in U.S. Pat. No. 5,350,410, to Kleks et al. is hereby incorporated herein by reference. It may also be noted that these features may also be included in the pacemaker contained in an ICD.

The systems described above thus represent a significant enhancement to pacemaker system longevity through minimization of current drain by operating at much lower safety factors. However, they automatically vary the amplitude or voltage of the stimulation pulse without looking at or taking into account the actual variation in current drain caused by a change in the voltage level of the stimulation pulse. Since capture is a function of energy delivered to the cardiac tissue, a more realistic manner of considering stimulation threshold is to view it as a continuous function described by the strength-duration relationship.

See, for example, Stokes and Bornzin, "The Electrode-Biointerface: Stimulation", Chapter 3 of *Modern Cardiac Pacing*, edited by S. Serge Barold, M.D. (Futura Publishing Co., 1985). The fundamental nature of the strength-duration relationship is that for very narrow pulse widths, a large stimulation pulse amplitude is required to obtain capture, and for wide pulse widths, a lower stimulation pulse amplitude is required to obtain capture. Thus, there is a wide variety of pulse amplitude and pulse width combinations which may be used to obtain capture at a given stimulation threshold. There are also a corresponding wide variety of pulse amplitudes and pulse widths combinations which may be used to provide an adequate safety factor.

However, the ability to independently program pulse amplitude and pulse width does not necessarily provide optimal pacing, because in order to maintain a desired or adequate safety factor, battery current drain is not considered as a primary factor. The first to note this was Bornzin in U.S. Pat. No. 5,697,956 (the '956 patent), which is assigned to the assignee of the present invention. Bornzin did not provide independent programming of pulse amplitude and pulse width, but rather provided only the programming of pulse energy, selected from a series of pulses of increasing or decreasing energy that had been selected to provide optimal pacing. This basic principle is the foundation of the present invention as well, and U.S. Pat. No. 5,697,956 is hereby incorporated herein by reference.

The technique taught in the '956 patent is a five step procedure which first determines the patient's strength-duration curve by determining a series of pulse thresholds for a particular patient as a function of a plurality of pulse widths. Second, desired pulse amplitude safety factor is added to the strength-duration curve to produce a plurality of pulse amplitude and pulse width combinations that would ensure capture at the desired safety factor. This may be thought of as a second curve identical to the strength-duration curve but displaced directly above it by an amount equal to the increase in voltage selected as a safety factor.

Third, a pulse current drain is computed as a function of each of the pulse amplitude and pulse width combinations determined in the second step. Fourth, a series of optimal pulse amplitude and pulse width combinations is selected that provides a minimal pacing current drain as a function of pacing energy. Fifth, the pacemaker is automatically programmed to the optimal pacing energy using the pulse amplitude and pulse width combination determined in the fourth step.

The procedure taught by the '956 patent represented a significant improvement over the previously used technique of manually programming the pacemaker to a desired pulse width, determining the voltage necessary to assure capture, and programming a higher voltage to provide a safety factor. For the first time, the pacing current required by the device was used as a guide to determine the pulse amplitude and the pulse width used. However, the '956 patent does not provide a method of optimization of such a device by the use of an automatic capture confirmation system. Nor does the system of the '956 patent truly determine optimal operating points, but rather it finds optimal points and adds a pulse amplitude (voltage) increment to such points which however, does not result in establishing optimal operating points.

It is a primary feature of the present invention to determine improved or optimal operating points from a battery current efficiency standpoint, and to operate the device at such operating points. In this regard, it is an objective of the present invention to determine those pulse amplitude/pulse width combinations that have the lowest battery drain of such combinations.

SUMMARY OF THE INVENTION

Briefly, the present invention determines improved or optimal operating points (stimulation pulse amplitude and stimulation pulse width combinations, hereinafter pulse amplitude/pulse width combinations) from an efficiency standpoint, as measured by battery charge drained from the battery. These operating points vary widely in the pacing energy that they deliver to cardiac tissue, and, as such, offer a complete array of pulse amplitude/pulse width combinations suitable to meeting the pacing thresholds of virtually any patient. Following the determination of these operating points, the pacing system is operated such that it paces at these operating points.

In one embodiment, the determination of the operating points is made by determining which of all of the possible pulse amplitude/pulse width combinations have the lowest battery charge drain at a predetermined level of stimulation efficacy. The level of stimulation efficacy required varies from patient to patient, and will also vary in the same patient over a period of time. The objective is thus to determine and utilize a quantifiable measure of stimulation efficacy.

DESCRIPTION OF THE DRAWINGS

These and other advantages of the present invention are best understood with reference to the drawings, in which:

FIG. 3 is an array containing battery charge drain values associated with various pulse amplitudes and pulse widths;

FIG. 4 is an array correlating the array of shown in FIG. 3 which contains the rheobase voltage values Vb associated with the various pulse amplitudes and pulse widths for a tissue chronaxie c with a value of 0.4 milliseconds, with the highlighted rheobase values representing stimulation pulse settings with the minimum charge for a given rheobase voltage value;

FIG. 5 is an array correlating to the array illustrated in FIG. 3 which contains the rheobase voltage values Vb associated with the various pulse amplitudes and pulse widths for a tissue chronaxie c with a value of 0.2 milliseconds, with the highlighted rheobase values representing stimulation pulse settings with the minimum charge for a given rheobase voltage value;

FIG. 6 is an array correlating to the array illustrated in FIG. 3 which contains the rheobase voltage values Vb associated with the various pulse amplitudes and pulse widths for a tissue chronaxie c with a value of 0.6 milliseconds, with the highlighted rheobase values representing stimulation pulse settings with the minimum charge for a given rheobase voltage value;

FIG. 7 is a table containing the highlighted rheobase voltage values Vb from the array of FIG. 4 from 0 to 7.5v for a tissue chronaxie c with a value of 0.4 milliseconds, together with the various pulse amplitudes and pulse widths each of the rheobase voltage values Vb is associated with;

DETAILED DESCRIPTION OF THE PREFERRED EMBODIMENTS

The preferred embodiment of the present invention will be described herein in exemplary fashion with reference to a dual-chamber pacemaker. While a dual-chamber device has been chosen for teaching purposes, it will at once be recognized by those skilled in the art that the present invention could also be implemented into a single-chamber pacemaker, or a single-chamber or dual-chamber ICD having a pacemaker incorporated therein.

Figure 1:
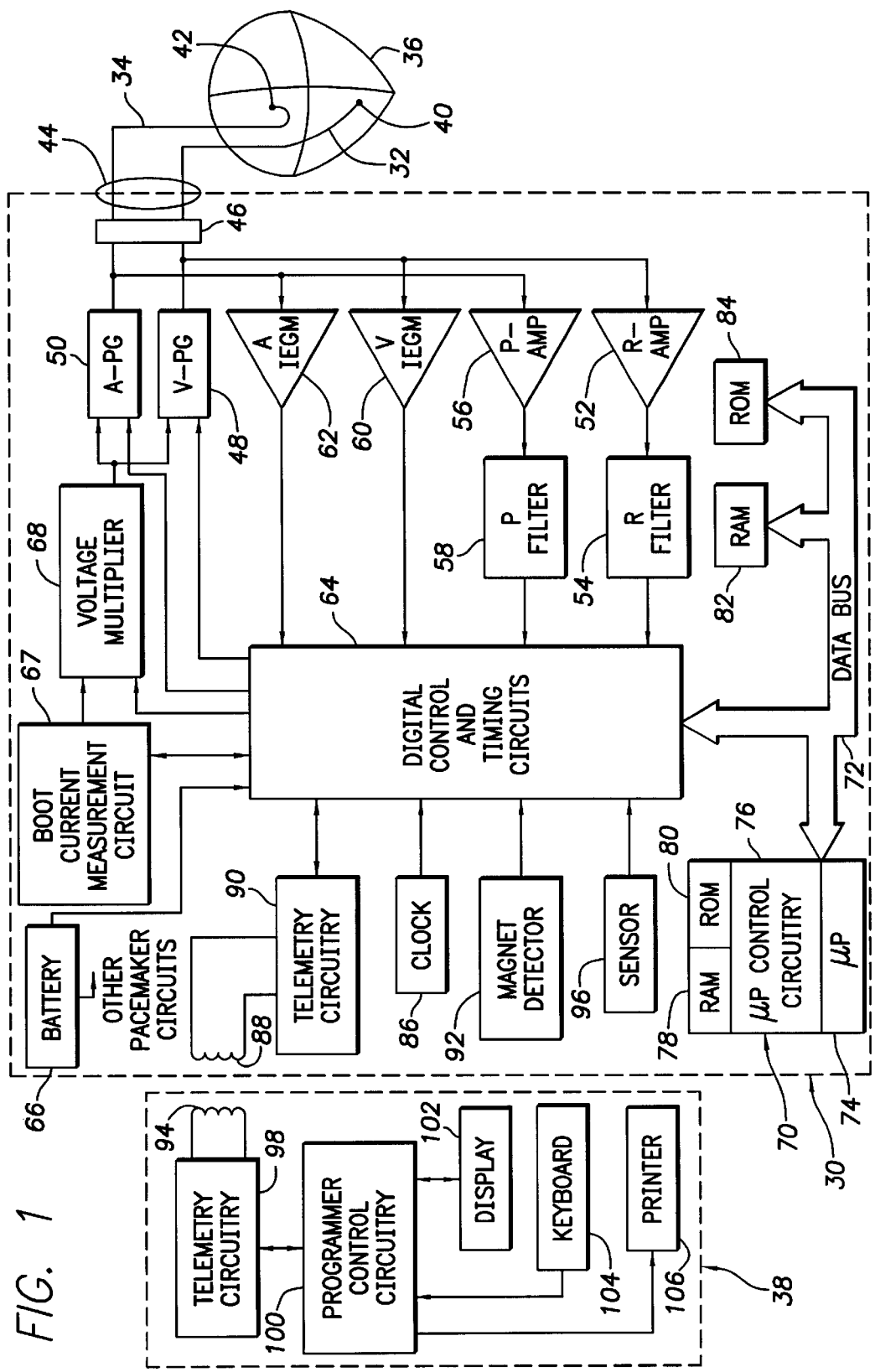
FIG. 1 is a functional block diagram of a pacemaker system in which the capture assurance system of the present invention can be implemented, showing a pacemaker, a programmer, and two pacing leads which are implanted in a heart.

Referring first to FIG. 1, a simplified block diagram of the circuitry needed for a dual-chamber pacemaker system is illustrated. The system includes a dual-chamber pacemaker 30, a ventricular pacing lead 32 and an atrial pacing lead 34, which leads are implanted with their distal portions placed in the respective chambers of a heart 36, and an external programmer 38 which is used to interrogate and program the pacemaker 30.

The ventricular pacing lead 32 has at least one electrode 40 which is in contact with one of the ventricles of the heart 36, and the atrial pacing lead 34 has at least one electrode 42 which is in contact with one of the atria of the heart 36. The leads 32 and 34 are electrically and physically connected to the pacemaker 30 through a connector 44 which forms an integral part of the device housing or "can" in which the circuitry and other components of the pacemaker 30 are housed.

The connector 44 is electrically connected to a protection network 46, which is used to electrically protect the circuits within the pacemaker 30 from excessive shocks or voltages which may appear on the electrodes 40 and/or 42 from a defibrillation shock.

The leads 32 and 34 carry stimulating pulses to the electrodes 40 and 42, respectively, from a ventricular pulse generator 48 and an atrial pulse generator 50, respectively. Further, electrical signals from the ventricle of the heart 36 are sensed by the electrode 40, and pass through the ventricular pacing lead 32 as an input to a ventricular channel sense amplifier 52, where they are amplified. The amplified signals from the ventricle are then supplied to a ventricular filter 54, where they are bandpass filtered.

Similarly, electrical signals from the atrium of the heart 36 are sensed by the electrode 42, and pass through the atrial pacing lead 34 as an input to an atrial channel sense amplifier 56, where they are amplified. The amplified signals from the atrium are then supplied to an atrial filter 58, where they are bandpass filtered.

The electrical signals from the ventricle are also supplied as an input to a ventricular IEGM (intracardiac electrogram) amplifier 60, which amplifies them. The ventricular IEGM amplifier 60 may be a digital amplifier, providing the digitized ventricular IEGM as an output. The ventricular IEGM typically may be telemetered out of the pacemaker 30 to the programmer 38, where it may be viewed. The ventricular IEGM amplifier 60 may also be configured to detect an evoked ventricular response from the heart 36 in response to an applied stimulation pulse, thereby aiding in the detection of ventricular capture.

The electrical signals from the atrium are also supplied as an input to an atrial IEGM (intracardiac electrogram) amplifier 62. The atrial IEGM amplifier 62 may be a digital amplifier, providing the digitized atrial IEGM as an output. The atrial IEGM typically may be telemetered from the pacemaker 30 to the programmer 38, where it may be viewed. The atrial IEGM amplifier 62 may also be configured to detect an evoked atrial response from the heart 36 in response to an applied stimulation pulse, thereby aiding in the detection of atrial capture.

The filtered, amplified signals from the ventricle (from the ventricular filter 54), the filtered, amplified signals from the atrium (from the atrial filter 58), the ventricular IEGM (from the ventricular IEGM amplifier 60), and the atrial IEGM (from the atrial IEGM amplifier 62) are all supplied as inputs to digital control and timing circuits 64. The digital control and timing circuits 64 are also connected to drive the ventricular pulse generator 48 and the atrial pulse generator 50. The digital control A battery 66 supplies electrical power to the digital control and timing circuits 64 and to a current measurement circuit 67 which is coupled to voltage multiplier 68, as well as to other circuitry within the pacemaker 30. The voltage multiplier 68 is controlled by the digital control and timing circuits 64, and supplies either one, two, or three times the voltage of the battery 66 (nominally 2.8 Volts) to the ventricular pulse generator 48 and the atrial pulse generator 50. This enables the ventricular pulse generator 48 and the atrial pulse generator 50 to provide pulse amplitudes greater than the battery voltage (typically the maximum pulse amplitude is approximately 7.5 Volts).

The digital control and timing circuits 64 generate pulse amplitude, pulse width, and trigger signals that are sent to the ventricular pulse generator 48 and the atrial pulse generator 50 for controlling the shape of the stimulation pulse provided by such generators. The trigger signals initiate the generation of stimulation pulses by the ventricular pulse generator 48 and the atrial pulse generator 50. The digital control and timing circuit 64 can also monitor the resulting pacemaker battery current drain as measured by the battery current measurement circuit 67, which includes the house keeping current as well as the current used in the pacing of the atrial and ventricular chambers of the heart. The resultant current measurement is available to the microprocessor 74 and the programmer 38.

During the time that either a ventricular pulse or an atrial pulse is being delivered to the heart 36, the corresponding amplifier (the ventricular channel sense amplifier 52 or the atrial channel sense amplifier 56) is typically disabled by way of a blanking signal presented to these amplifiers from the digital control and timing circuits 64. This blanking action prevents the ventricular channel sense amplifier 52 and the atrial channel sense amplifier 56 from becoming saturated from the relatively large stimulation pulses that are present at their input terminals during this time. This blanking action also helps prevent residual electrical signals present in the muscle tissue as a result of the pacemaker stimulation from being interpreted as P-waves or R-waves.

In the preferred embodiment, the pacemaker 30 is controlled by a microprocessor circuit 70 which is programmed to carry out control and timing functions. The microprocessor circuit 70 is coupled to the digital control and timing circuits 64 with a data communication bus 72. The microprocessor circuit 70 typically includes a microprocessor 74, microprocessor control circuitry 76, and an on-board RAM 78 and an onboard ROM 80. The microprocessor control circuitry 76 typically includes an on-board system clock. The microprocessor circuit 70 is typically fabricated using a custom low-power microprocessor and standard or custom RAM and ROM components.

Also controlled by the microprocessor 74 are an off-board RAM 82 and an off-board ROM 84, both of which are coupled to the microprocessor circuit 70 by the data communication bus 72. The offboard RAM 82 can be a single RAM element, or it may be several discrete RAM elements, each of which is coupled to the data communication bus 72. Similarly, the off-board ROM 84 can be a single ROM element, it is may also be several discrete ROM elements, each of which is coupled to 72. The off-board RAM 82 may also be subdivided into as many different memory blocks or sections (addresses) as needed in order to allow desired data and control information to be stored.

The off-board RAM 82, and/or the on-board RAM 78, allow certain control parameters to be programmably stored and modified, as required, in order to customize the pacemaker's operation to suit the needs of a particular patient. Further, data sensed during the operation of the pacemaker may be stored in the off-board RAM 82, and/or the on-board RAM 78, for later retrieval and analysis.

Representative of the types of control systems which may be used with the present invention is the microprocessor-based control system described in U.S. Pat. No. 4,940,052, to Mann, et al. Reference is also made to U.S. Pat. No. 4,712,555, to Thornander, et al. and U.S. Pat. No. 4,944,298, to Sholder, wherein a state-machine type of operation for a pacemaker is described, and U.S. Pat. No. 4,788,980, to Mann, et al. wherein the various timing intervals used within the pacemaker and their inter-relationship are more thoroughly described. U.S. Pat. Nos. 4,940,052, 4,712,555, 4,944,298, and 4,788,980 are hereby each incorporated herein by reference.

A clock circuit 86, which is typically a crystal-controlled oscillator, provides main timing clock signals to the digital control and timing circuits 64, with the clock signals being supplied to other circuits making use of them through the data communication bus 72.

RF (radio frequency) signals are exchanged between the pacemaker 30 and the programmer 38, and are received and transmitted by the pacemaker 30 using an antenna 88 which is connected to telemetry circuitry 90, which is in turn connected to the digital control and timing circuits 64.

Advantageously, by using the programmer 38, desired commands may be telemetrically sent to the pacemaker 30, and data such as device parameters and device history from the pacemaker 30 may be received and displayed by the programmer 38.

The telemetry circuitry 90 may be of conventional design, such as is described in U.S. Pat. No. 4,944,299, to Silvian, or as is otherwise known in the art. U.S. Pat. No. 4,944,299 is hereby incorporated herein by reference.

The pacemaker 30 further includes a magnet detector 92, which provides a signal indicating when a magnet is placed over the pacemaker 30. The magnet may be used by a physician, other medical personnel, or the pacemaker patient to perform various reset functions of the pacemaker 30, and/or to indicate that a telemetry wand 94 of the programmer 38 is in place to receive data from, or send data to the pacemaker 30.

As needed for certain applications, the pacemaker 30 may further include at least one sensor 96 which is operatively connected to the digital control and timing circuits 64. A common type of sensor is an activity sensor, such as an accelerometer, which may be mounted on the circuitry of the pacemaker 30, or a piezoelectric crystal, which may be mounted to the case of the pacemaker 30.

Other types of sensors are also known, such as sensors which sense respiration rate, the oxygen content of blood, the pH of blood, the temperature of blood, the QT interval, body motion, and the like. Any sensor or combination of sensors capable of sensing a physiological or physical parameter relatable to the rate at which the heart should be beating (i.e., relatable to the metabolic need of the patient) can be used. Such sensors are commonly used with "rate-responsive" pacemakers in order to adjust the pacemaker rate (the frequency of delivery of the stimulation pulses) in a manner which tracks the physiological or metabolic needs of the patient.

Referring now to the programmer 38, the telemetry wand 94 is connected to programmer telemetry circuitry 98. The programmer telemetry circuitry 98 is in turn operatively connected to programmer control circuitry 100, which includes memory therein. A touch screen display 102 is operatively connected to the programmer control circuitry 100 to both display information from the programmer control circuitry 100 and to provide input signals to the programmer control circuitry 100.

A keyboard 104 is operatively connected to the programmer control circuitry 100 to provide input signals to the programmer control circuitry 100, and a printer 106 is operatively connected to the programmer control circuitry 100 to provide a permanent record of device parameters and operations. A more complete exemplary description of a programmer is given in U.S. Pat. No. 4,809,697, to Causey, III, et al., which patent is hereby incorporated herein by reference.

The principle which the capture assurance pacing system of the present invention utilizes is that of determining a set of optimal pulse amplitudes and pulse widths, which are defined by determining the pairs of pulse amplitude and pulse width which provide the greatest rheobase voltage at minimum charge drain from the battery 66. The selected pairs of pulse amplitude and pulse width are then organized into a table for later retrieval and use; only those pairs of pulse amplitude and pulse width which are listed in the table will be used in the operation of the device.

Figure 2:
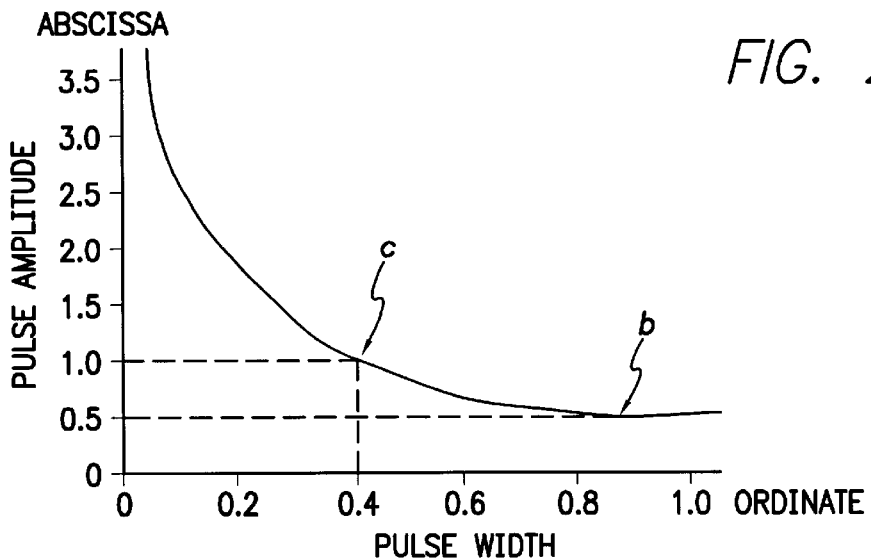
FIG. 2 is a strength-duration curve which has pulse duration plotted on the horizontal coordinate, and pulse amplitude plotted on the vertical coordinate.

In order to understand the principles of the present invention, it is necessary to fully understand the parameters associated with the strength-duration curve. Referring now to FIG. 2, a strength-duration curve is illustrated with pulse duration plotted on the ordinate, and pulse amplitude plotted on the abscissa. The strength-duration curve is a graphical representation of the relationship between pulse amplitude and pulse width to achieve capture.

There exists a point b on the strength-duration curve that is called the rheobase, which represents the lowest pulse amplitude at which capture will occur, with no further improvement being obtained by a further increase in pulse width. Thus, in FIG. 2, it may be seen that the rheobase b is approximately 0.5 Volts.

At another point on the strength-duration curve, the pulse amplitude is two times the value of the rheobase b. The pulse width associated with such point on the strength-duration curve is known as the chronaxie or chronaxie time (which is represented by the character c). For the strength-duration curve of FIG. 2, it is observed that the chronaxie c is approximately 0.4 milliseconds. Typical values for the chronaxie c for pacing range from 0.2 milliseconds to 0.6 milliseconds.

For purposes of the following discussion it is assumed that the pacing pulse can be approximated by a rectangular pulse having an amplitude V and a duration of d. Other waveforms can be used without departing from the spirit of the invention. By establishing values for a given patient for the rheobase b and the chronaxie c, the entire strength-duration curve may be computed by using the Weiss-Lapicque strength-duration mathematical description:

$$V=b*(1+c/d) \quad (1)$$

where b is the rheobase, c is the chronaxie, V is the pulse amplitude, and d is the pulse width or duration. By solving for the rheobase b, the equation may be rewritten as:

$$b=V/(1+c/d) \quad (2)$$

This relationship is one of two which are key to the capture assurance pacing system of the present invention.

The other relationship which is key to the present invention is the equation relating the amount of charge delivered from the battery 66 to the patient:

$$Q=(V/R)*d (\text{for } V \leq 2.5V) \quad (3)$$

$$Q=2*(V/R)*d (\text{for } 2.5V<V \leq 5.0V) \quad (4)$$

$$Q=3*(V/R)*d (\text{for } 5.0V<V \leq 7.5V) \quad (5)$$

where Q is the amount of charge delivered, R is the combined impedance of the lead and cardiac tissue, V is the pulse amplitude, and d is the pulse width or duration. The third equation is used when the pulse amplitude to be delivered is low enough to be delivered directly from the battery 66 voltage, the fourth equation is used when the pulse amplitude requires the voltage multiplier 68 (illustrated in FIG. 1) to double the voltage of the battery 66, and the fifth equation is used when the pulse amplitude requires the voltage multiplier 68 to triple the voltage of the battery 66. The lead/tissue impedance R typically ranges from 200 Ohms to 1000 Ohms, with 500 Ohms being a nominal value.

The next step in understanding the operation of the capture assurance pacing system of the present invention involves establishing two tables, one table being a tabulation of charge delivered as a function of pulse amplitude and pulse width and the second table being a tabulation of rheobase as a function of pulse amplitude and pulse width.

An example of the first type of table is shown in FIG. 3. Note that FIG. 3 shows pulse amplitudes varying up to 7.5 Volts, in which case the voltage multiplier 68 would have capability to only triple the voltage of the battery 66. For the table illustrated in FIG. 3, the lead/tissue impedance R is assumed to be 500 Ohms.

An example of the second type of table is illustrated in FIG. 4. For the table illustrated in FIG. 4, the chronaxie c is assumed to be 0.4 milliseconds. As in the case of the table of FIG. 3, the table of FIG. 4 shows pulse amplitudes varying only up to 5.0 Volts.

The tables of FIGS. 3 and 4 are then compared to determine a sequence of pulse amplitude/pulse width combinations which progressively increase in both rheobase value and stimulation pulse energy content. Each of the pulse amplitude/pulse width combinations in the sequence must have the lowest battery charge drain of any pulse amplitude/pulse width combination having at least the rheobase value of that particular pulse amplitude/pulse width combination.

By repeating this comparison for each pulse amplitude/pulse width pair, and by removing any pairs which require a higher amount of charge Q than another pair delivering a higher rheobase b for the same or less charge Q, all of the pairs of data points may be selected. In FIGS. 3 and 4, the pairs of data points so selected are shown in shaded areas.

FIG. 5 shows the values of the rheobase b for all of the varying pulse amplitudes and pulse widths which can be delivered with the value of the chronaxie c assumed to be 0.2 milliseconds. FIG. 5 shows pulse amplitudes varying up to 5.0 Volts. The optimal pairs of data points for this value of the chronaxie c are shown in shaded areas in FIGS. 5 and 6.

Similarly, FIG. 6 shows the values of the rheobase b for all of the varying pulse amplitudes and pulse widths which can be delivered with the value of the chronaxie c assumed to be 0.6 milliseconds. FIG. 6 shows pulse amplitudes varying up to 5.0 Volts. The optimal pairs of data points for this value of the chronaxie c are shown in shaded areas in FIG. 6.

FIGS. 3 and 4 show pulse amplitudes varying up to 7.5 Volts, in which case the voltage multiplier 68 would have capability to treble the voltage of the battery 66. FIG. 3 shows a plot of the charge Q delivered from the battery 66 for all of the varying pulse amplitudes and pulse widths. FIG. 4 shows a plot of the values of the rheobase b for all of the varying pulse amplitudes and pulse widths which can be delivered with the value of the chronaxie c assumed to be 0.4 milliseconds. The optimal pairs of data points for this value of the chronaxie c are shown in shaded areas in FIGS. 3 and 4.

In practice, it has been determined that the optimal pairs of data points begin in the upper left corner of the tables at a pulse width (PW) of 0.2 milliseconds, and a pulse amplitude (PA) of 0.5 Volts. This combination of minimum values represents the minimum battery charge drain (0.2 microCoulombs) for each stimulation pulse. Referring to FIGS. 3 and 4 for exemplary purposes, the progression of data points goes down the left-most column to the data point at 0.2 milliseconds, 2.5 volts (1.0 microCoulombs for a 0.83 Volt rheobase). The 2.5 volt value represents the highest voltage obtainable from the battery 66 without using the voltage multiplier (since pacemaker batteries typically have a nominal voltage which is sufficient to generate this pulse amplitude without the use of a voltage multiplier). Also included in FIGS. 3 and 4 in serial fashion, are determinations for a 5.0 volt and 7.5 volt battery source accomplished typically using a voltage doubler and tripler respectively.

The next data point established in FIG. 3 is located in the next column to the right (0.4 milliseconds) by locating the first data point which has a higher rheobase value b, than the previous value (2.5 volts, at which point the charge drained is 1.40 microCoulombs for a 0.88 Volt rheobase). The progression of data points then again goes down to the data point at 2.5 volts. This process continues to the additional columns to the right, each time going down to 2.5 volts.

When the data point at 1.6 milliseconds, 2.5 volts is reached (at which the charge drained is 8 microCoulombs for a 2.00 Volts rheobase), the next data point will be the data point with the first rheobase value above 2.00 Volts. That point is 0.4 milliseconds, 4.25 Volts. The process then continues to determine all of the data points which are shaded in FIGS. 3 and 4, the last of which is 1.6 milliseconds, 7.5 Volts (at which the charge drained is the ventricular pacing lead 72 microCoulombs for a 6.00 Volt rheobase). These shaded data points are the only pairs of pulse stimulation amplitude and pulse width at which the device will be operated.

The optimal pulse amplitude/pulse width combinations illustrated in FIGS. 3 and 4 have been entered into a single table in FIG. 7. Since it may be noted from the table of FIG. 7 that there are several occasions in which the variation of the rheobase b from one pair of pulse amplitude/pulse width combinations to the next is relatively small (for example, from 0.83 Volts to 0.88 Volts), it may be desirable to eliminate those data points which do not produce a minimal variation in the rheobase. Those skilled in the art will readily appreciate how to accomplish this expeditiously.

A first implementation of the present invention would be to have the pacemaker permanently programmed to pulse amplitude/pulse width combinations based upon a standard chronaxie c value. For example, the typical value of the chronaxie c is 0.4 millisecond. By selecting this value, the values of the pulse amplitude/pulse width combinations for the pacemaker can be determined.

Figure 8:
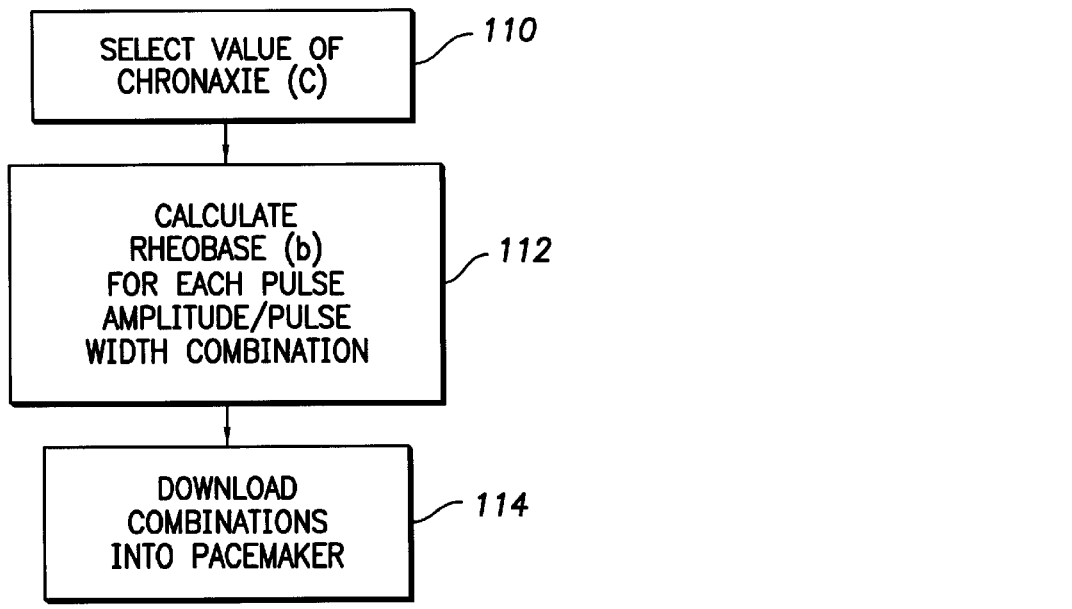
FIG. 8 is a flow chart which provides an overview of a method which may be used by the present invention to manually select a value of the chronaxie c and program a corresponding sequence of optimal program pulse amplitudes and pulse widths into the pacemaker memory.

A second implementation allows the physician to program the value of the chronaxie c into the pacemaker system. This can be accomplished in two different ways. The first of these two ways is illustrated in FIG. 8, that depicts a process in which, after a prescribed value of the chronaxie is programmed into the programmer 38, the programmer is used to calculate and select the optimal pulse amplitude/pulse width combinations, which are then downloaded into the pacemaker. The pacemaker 30, like virtually all such devices at present, is capable of measuring the lead/tissue impedance R. This value enables the values of charge delivered (Q) to be calculated as shown, for example, in FIG. 3. Furthermore, the pacemaker 30 can also measure its own internal current drain from battery 66 as monitored by the current measurement circuit 67.

In block 110, the physician enters a value for the chronaxie c into the programmer 38 and based upon this value the programmer 38 will calculate all of the values in the rheobase table (e.g., FIG. 4) in block 112. Also in block 112, the programmer 38 calculates the optimal values of the pulse amplitude/pulse width combinations. The optimal values of the pulse amplitude/pulse width combinations are then telemetered into the pacemaker 30 in block 114, where they are programmed into memory (such as RAM 82).

Figure 9:
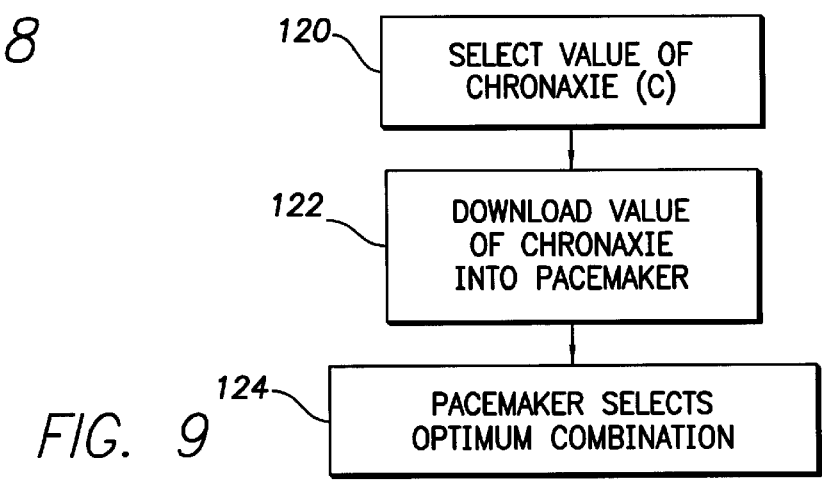
FIG. 9 is a flow chart which provides an overview of a method which may be used by the present invention to manually select a value of the chronaxie c and program that value into the pacemaker, which selects a corresponding sequence of optimal program pulse amplitudes and pulse widths stored in the pacemaker memory.

The second way in which the physician can program the value of the chronaxie c into the pacemaker system is illustrated in FIG. 9. In block 120, the physician selects a value for the chronaxie c from a plurality of values which may be chosen using the programmer 38. The selected value of the chronaxie c is then telemetered into the pacemaker 30 in block 122. In block 124, the pacemaker 30 uses the selected value of the chronaxie c to select a corresponding one of a plurality of different sets of optimal values of the pulse amplitude/pulse width pairs (which are typically stored in the off-board ROM 84), with the selected set of optimal values being programmed into memory (RAM 82).

Figure 10:
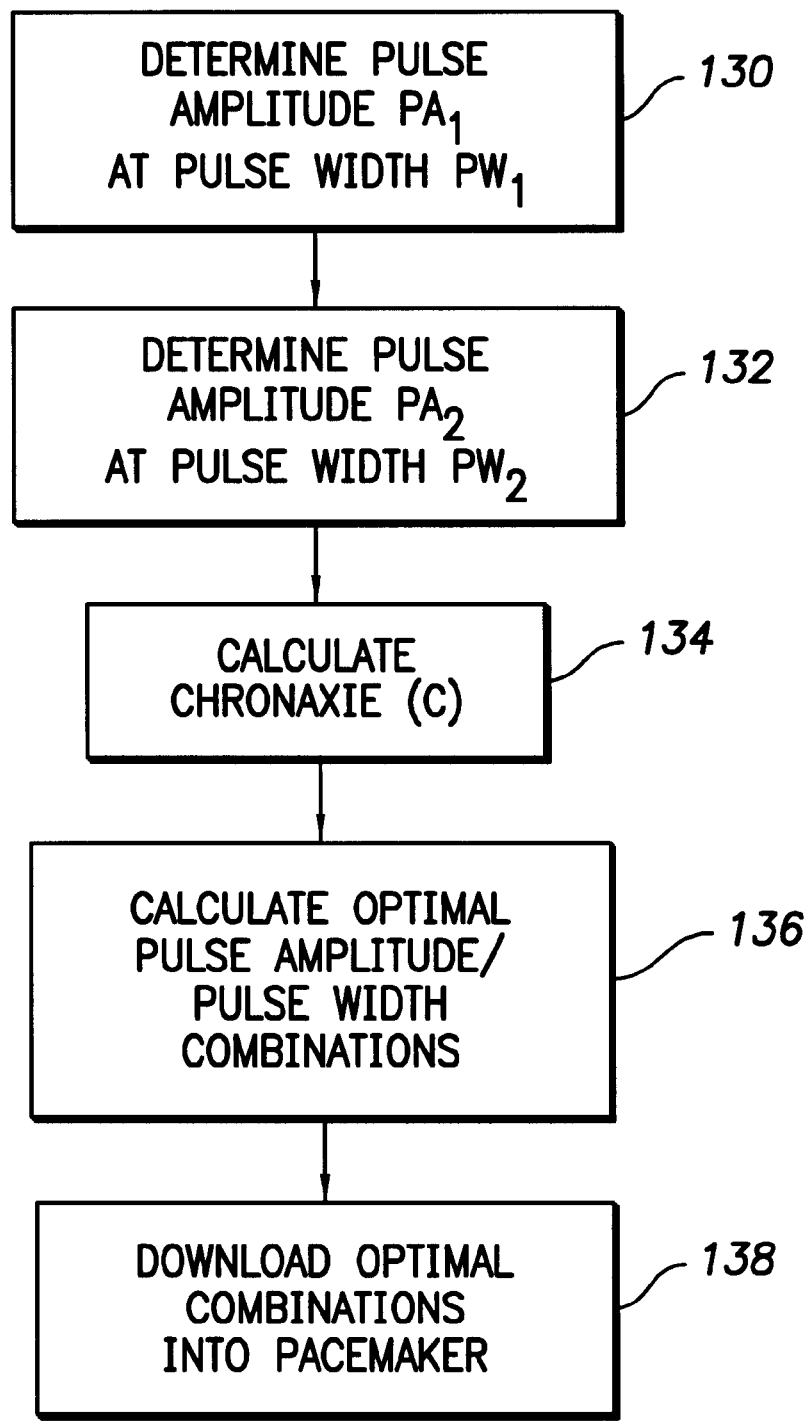
FIG. 10 is a flow chart which provides an overview of a method which may be used by the present invention to calculate a value of the chronaxie c and program a corresponding sequence of optimal program pulse amplitudes and pulse widths into the pacemaker memory.

A third implementation uses the programmer 38 to determine a value for the chronaxie c. This can be accomplished in two different ways. The first is illustrated in FIG. 10, which depicts a process in which the programmer 38 calculates the value of the chronaxie c, then the table values, and then selects the optimal pulse amplitude/pulse width combinations, which are then programmed into the pacemaker. In block 130, the programmer 38 operates the pacemaker 30 to determine a first pulse amplitude threshold V1 at a first pulse width d1. In block 132, the programmer 38 operates the pacemaker 30 to determine a second pulse amplitude V2 at a second pulse width d2.

These two data points are then used by the programmer 38 in block 134 to simultaneously solve two instances the following formula for the actual value of chronaxie c:

$$c = (PA1 - PA2)/(PA2/PW1 - PA1/PW2) \text{ where} \quad (6)$$

PA1=a first pulse amplitude at a first preselected pulse width (PW1) when capture is first obtained; and PA2=a second pulse amplitude at a second preselected pulse width (PW2) when capture first occurs. Based upon this value of the chronaxie c, the programmer 38 will calculate all of the values in the rheobase table (e.g., FIG. 4) in block 136. Also in block 136, the programmer 38 calculates the optimal values of the pulse amplitude/pulse width combinations. The optimal values of the pulse amplitude/pulse width combinations are then telemetered into the pacemaker 30 in block 138, where they are programmed into memory (RAM 82).

Figure 11:
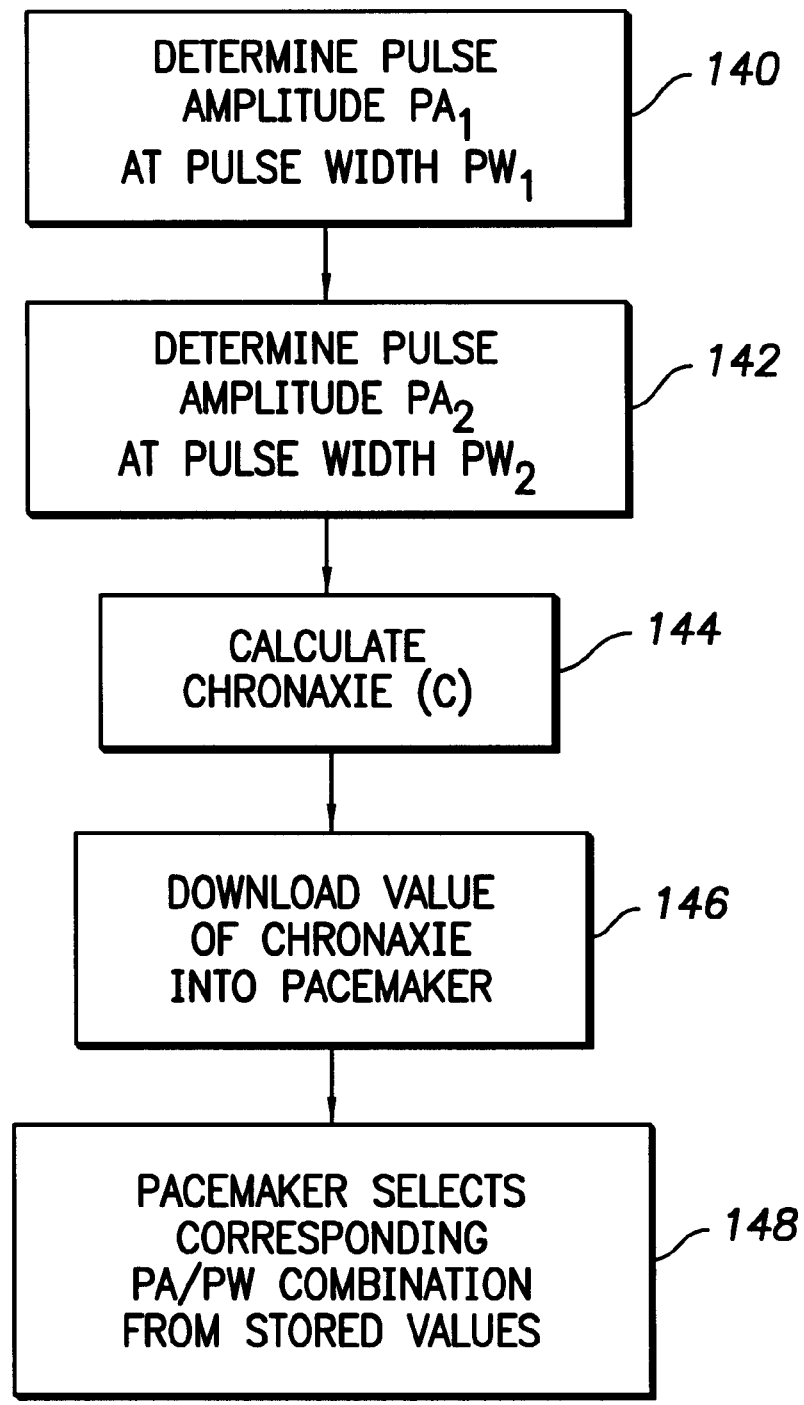
FIG. 11 is a flow chart which provides an overview of a method which may be used by the present invention to calculate a value of the chronaxie c and program that value into the pacemaker, which selects a corresponding sequence of optimal program pulse amplitudes and pulse widths stored in the pacemaker memory.

The second way in which the programmer 38 may be used to determine a value for the chronaxie c is illustrated in FIG. 11. In block 140, the programmer 38 operates the pacemaker 30 to determine a first pulse amplitude threshold V1 at a first pulse width d1. In block 142, the programmer 38 operates the pacemaker 30 to determine a second pulse amplitude V2 at a second pulse width d2.

These two data points are then used by the programmer 38 in block 144 to solve equation (6) above for the actual value of chronaxie c. The programmer 38 then telemeters the calculated value of the chronaxie c to the pacemaker 30 in block 146. In block 148, the pacemaker 30 uses the selected value of the chronaxie c to select a corresponding one of a plurality of different sets of optimal values of the pulse amplitude/pulse width combinations (again typically stored in the off-board ROM or Ram 84), with the selected set of optimal values being programmed into memory (RAM 82).

Figure 12:
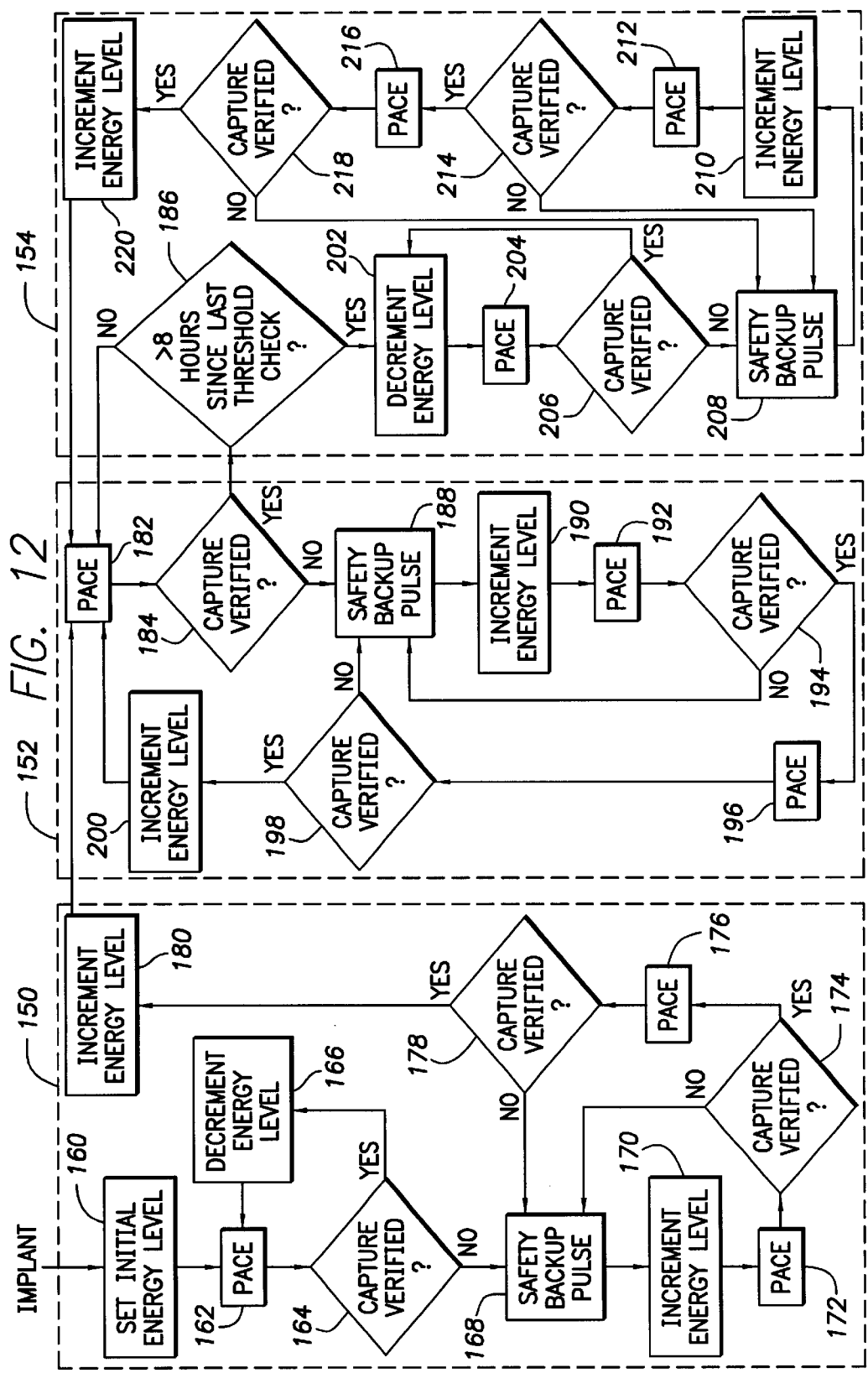
FIG. 12 is a flow chart which provides an overview of the method used by the present invention to automatically determine the optimal pacing energy, where "optimal" means a pacing energy designed to assure a desired safety factor while minimizing battery current drain.

Referring finally to FIG. 12 and using c=0.4 milliseconds, an overview of the method used by the improved pacing system of the present invention to automatically determine and maintain the optimal pacing energy is illustrated. The method illustrated in FIG. 12 is the preferred mode, and incorporates capture verification, issuance of a safety backup pulse, and automatic threshold determination. There are three modules shown in FIG. 12: an initial threshold determination module 150, a main pacing operation module 152, and a periodic threshold determination module 154. The initial threshold determination module 150 operates whenever the pacemaker 30 is initially implanted in a patient, or when the pacing system has been reset and must reinitialize its operation.

The pacemaker 30 sets an initial energy level in block 160, and then paces the patient in block 162. Capture is monitored in block 164, and if capture is verified, the pacing energy level is decreased in block 166 by selecting values for the pulse amplitude/pulse width pairs which are associated with the next lowest rheobase value selected from FIG. 7. After decreasing the pacing energy level, the device returns to pacing in the block 162, after which it attempts to verify capture in block 164. If capture is not verified in the block 164, the process is diverted to block 168, where a safety backup pulse is delivered (safety backup pulses are typically delivered at 4.5 Volts to ensure capture).

Following delivery of a safety backup pulse in block 168, the pacing energy level is increased in block 170 by selecting values for the pulse amplitude/pulse width which are associated with the next highest rheobase value from FIG. 7. The pacemaker 30 then paces the patient in block 172, and capture is monitored in block 174. If capture is not verified, the pacemaker 30 returns to the block 168. If capture is verified, the pacemaker 30 moves to block 176, where the patient is paced, and capture is verified in block 178.

If capture is not verified in block the 178, the pacemaker 30 returns to the block 168. If capture is verified (and thus has been verified for two consecutive beats at the selected values for the pulse amplitude and the pulse width), the pacemaker 30 moves to block 180, where the pacing energy level is increased by selecting values for the pulse amplitude/pulse width which are associated with the next highest rheobase value from FIG. 7 (for added safety margin).

It will be appreciated by those skilled in the art that in the initial threshold determination module 150, the values for the pulse amplitude/pulse width which are associated with the lowest rheobase value which captures the patient's cardiac tissue are determined. Following this determination, a safety factor is added to the pacing operation in the block 180 by setting the values for the pulse amplitude/pulse width to those values which are associated with the next highest rheobase value.

Optionally, the values associated with the second or even third higher rheobase value could also be used to increase the safety factor. Such an added increase (beyond increasing one rheobase value) is believed to be unnecessary in the preferred embodiment since the pacemaker 30 has both capture verification and safety backup pulse capability. The operation of the initial threshold determination module 150 is used when the pacemaker 30 is first implanted, or when a system reset occurs.

The normal pacing operation of the pacemaker 30 is contained in the main pacing operation module 152, which may be entered from the block 180 in the initial threshold determination module 150. The pacemaker 30 paces the patient in block 182, and then monitors capture in block 184. If capture is verified in the block 184, the system moves to the periodic threshold determination module 154, where in block 186 a determination is made whether or not eight hours has elapsed since the last time that the patient's threshold was checked in the periodic threshold determination module 154.

If it has been less than eight hours since the patient's threshold was last checked, the system returns to the block 182 in the main pacing operation module 152. The three blocks of pacing in the block 182, verifying capture in the block 184, and checking to determine whether sufficient time has elapsed to check threshold in the block 186 comprise the normal operating routing of the pacemaker 30. The procedure to be followed if eight hours have elapsed since the patient's threshold was last checked will be discussed below in conjunction with the discussion of the periodic threshold determination module 154.

If capture is not verified in the block 184, the process is diverted to block 188, where a safety backup pulse is delivered. Following delivery of a safety backup pulse in block 188, the pacing energy level is increased in block 190 by selecting values for the pulse amplitude/pulse width which are associated with the next highest rheobase value FIG. 7. The pacemaker 30 then paces the patient in block 192, and capture is monitored in block 194. If capture is not verified, the pacemaker 30 returns to the block 188. If capture is verified, the pacemaker 30 moves to block 196, where the patient is paced, and capture is verified in block 198.

If capture is not verified in the block 198, the pacemaker 30 returns to the block 188. If capture is verified(and has again been verified for two consecutive beats at the selected values for the pulse amplitude and the pulse width), the pacemaker 30 moves to block 200, where the pacing energy level is increased by selecting values for the pulse amplitude/pulse width which are associated with the next highest rheobase value from FIG. 7. This adds a safety factor to the pacing operation by setting the values for the pulse amplitude/pulse width to those values which are associated with the next highest rheobase value.

As mentioned above, a threshold test is run periodically (every eight hours in the preferred embodiment) in order to determine whether the stimulation threshold has decreased in the periodic threshold determination module 154. If it is determined in the block 186 that eight hours have elapsed since the last time that the threshold was checked, operation of the pacemaker 30 moves to block 202, where the pacing energy level is deceased by selecting values for the pulse amplitude/pulse width which are associated with the next lowest rheobase value from FIG. 7.

After decreasing the pacing energy level, the device returns to pacing in the block 204, after which it attempts to verify capture in block 206. If capture is not verified in the block 206, the process is diverted to block 208, where a safety backup pulse is delivered. Following delivery of a safety backup pulse in block 208, the pacing energy level is increased in block 210 by selecting values for the pulse amplitude/pulse width which are associated with the next highest rheobase value from FIG. 7. The pacemaker 30 then paces the patient in block 212, and capture is monitored in block 214. If capture is not verified in the block 214, the pacemaker 30 returns to the block 208. If capture is verified, the pacemaker 30 moves to block 216, where the patient is paced, after which capture is verified in the block 218.

If capture is not verified in the block 218, the pacemaker 30 returns to the block 208. If capture is verified(and has again been verified for two consecutive beats at the selected values for the pulse amplitude and the pulse width), the pacemaker 30 moves to block 220, where the pacing energy level is increased by selecting values for the pulse amplitude/pulse width which are associated with the next highest rheobase value from FIG. 7. This adds a safety factor to the pacing operation by setting the values for the pulse amplitude/pulse width to those values which are associated with the next highest rheobase value. The operation then returns to the block 182 in the main pacing operation module 152.

Although an exemplary embodiment of the improved pacing system of the present invention has been shown and described with reference to particular embodiments and applications thereof, it will be apparent to those having ordinary skill in the art that a number of changes, modifications, or alterations to the invention as described herein may be made, none of which depart from the spirit or scope of the present invention. All such changes, modifications, and alterations should therefore be seen as being within the scope of the present invention.

What is claimed is:

1. An implantable cardiac stimulation device capable of providing pacing therapy, the implantable cardiac stimulation device comprising:

a first memory that is capable of storing a plurality of pulse amplitude/pulse width combinations each of which is associated with a rheobase value and a stimulation pulse energy content, wherein each of the pulse amplitude/pulse width combinations has the lowest battery charge drain of any possible pulse amplitude/pulse width combination having at least the rheobase value of that particular pulse amplitude/pulse width combination;

control circuitry, operatively connected to the first memory, that is operative to select a pulse amplitude/pulse width combination;

a stimulation pulse generator that is operative to generate stimulation pulses at the selected pulse amplitude/pulse width combination, at prescribed times upon demand, to stimulate cardiac tissue; and an automatic capture detector which detects and provides an output indicative of whether the stimulation pulses obtain capture of cardiac tissue, the output of the automatic capture detector being supplied to the control circuitry, the control circuitry causing the stimulation pulse generator to generate stimulation pulses at the selected pulse amplitude/pulse width combination if the stimulation pulses obtain capture of cardiac tissue, the output of the automatic capture detector causing the stimulation pulse generator to generate stimulation pulses at another pulse amplitude/pulse width combination from the first memory which is associated with an incrementally higher rheobase value and stimulation pulse energy content to obtain capture with a safety margin.

2. An implantable cardiac stimulation device as defined in claim 1, wherein the plurality of pulse amplitude/pulse width combinations are permanently programmed into the first memory.

3. An implantable cardiac stimulation device as defined in claim 1, additionally comprising:

telemetry circuitry, coupled to the control circuitry, for establishing a telemetry link with an external programming unit, and for facilitating the transfer of the plurality of pulse amplitude/pulse width combinations into the first memory.

4. An implantable cardiac stimulation device as defined in claim 3, additionally comprising:

a second memory, the second memory containing at least two different pluralities of pulse amplitude/pulse width combinations, the external programmer being operable to cause one of the two different pluralities of pulse amplitude/pulse width combinations to be supplied from the second memory to the first memory for storage therein.

5. An implantable cardiac stimulation device as defined in claim 4, wherein the second memory is located in the implantable cardiac stimulation device.

6. An implantable cardiac stimulation device as defined in claim 4, wherein the second memory is located in the external programming unit.

7. An implantable cardiac stimulation device as defined in claim 4, wherein each of the different pluralities of pulse amplitude/pulse width combinations is associated with one of a corresponding different chronaxie values, a specific one of which may be selected by an operator of the external programming unit.

8. An implantable cardiac stimulation device as defined in claim 4, wherein each of the different pluralities of pulse amplitude/pulse width combinations is associated with one of a corresponding different chronaxie values, wherein the particular one of the plurality of sequences to be used is determined by threshold testing of the patient to determine pulse amplitude threshold at at least two different pulse widths.

9. An implantable cardiac stimulation device as defined in claim 3, additionally comprising:

means for calculating the plurality of pulse amplitude/pulse width combinations based upon a value of chronaxie.

10. An implantable cardiac stimulation device as defined in claim 9, wherein the value of chronaxie is entered by an operator of the external programming unit.

11. An implantable cardiac stimulation device as defined in claim 9, wherein the value of chronaxie is determined by threshold testing of the patient to determine pulse amplitude threshold at at least two different pulse widths.

12. An implantable cardiac stimulation device as defined in claim 9, wherein the calculation of the plurality of pulse amplitude/pulse width combinations based upon a value of chronaxie occurs in the external programming unit, following which the plurality of pulse amplitude/pulse width combinations based upon the value of chronaxie entered by an operator of the external programming unit are transferred into the implantable cardiac stimulation device and stored in the first memory.

13. An implantable cardiac stimulation device as defined in claim 9, wherein the value of chronaxie entered by an operator of the external programming unit is transferred into the implantable cardiac stimulation device, where the control circuitry performs pulse amplitude/pulse width combination the calculation of the plurality of pulse amplitude/pulse width combinations and stores them in the first memory.

14. An implantable cardiac stimulation device as defined in claim 1, wherein rheobase value is calculated according to the formula $$b = V/(1+c/d)$$

where V is the pulse amplitude, d is the pulse width, and c is the tissue chronaxie.

15. An implantable cardiac stimulation device as defined in claim 1, wherein each pulse amplitude/pulse width combination is associated with a particular rheobase value which differs from the next lower rheobase value associated with a pulse amplitude/pulse width combination by at least a predetermined amount.

16. An implantable cardiac stimulation device as defined in claim 1, additionally comprising:
   a threshold detector which detects and provides an output indicative of which of the plurality of pulse amplitude/pulse width combinations has the lowest battery charge drain while still obtaining capture of cardiac tissue.

17. An implantable cardiac stimulation device as defined in claim 16, wherein the output of the threshold detector is supplied to the control circuitry, the control circuitry causing the stimulation pulse generator to generate stimulation pulses at one of the plurality of pulse amplitude/pulse width combinations which has the same or an incrementally higher rheobase value and stimulation pulse energy content as the pulse amplitude/pulse width combination determined by the threshold detector to have the lowest battery charge drain while still obtaining capture of cardiac tissue.

18. An implantable cardiac stimulation device as defined in claim 1, additionally comprising:
   a safety backup pulse generator which automatically causes the stimulation pulse generator to issue a high voltage safety backup stimulation pulse immediately following a detection by the capture detector of a failure of any stimulation pulse to obtain capture.

19. An implantable cardiac stimulation device as defined in claim 1, wherein the incrementally higher rheobase value and stimulation pulse energy content is the next highest rheobase value and stimulation pulse energy content from the first memory.

20. An implantable cardiac stimulation device capable of providing pacing therapy, the implantable cardiac stimulation device comprising:
   a memory that stores a plurality of pulse amplitude/pulse width combinations each of which is associated with a rheobase value and a stimulation pulse energy content, each of which pulse amplitude/pulse width combinations has the lowest battery charge drain of any possible pulse amplitude/pulse width combination having at least the rheobase value of that particular pulse amplitude/pulse width combination;
   control circuitry, operatively connected to the memory, that is operative to select one pulse amplitude/pulse width combination from the plurality of pulse amplitude/pulse width combinations;
   a stimulation pulse generator that generates stimulation pulses at the selected pulse amplitude/pulse width combination, at prescribed times upon demand, to stimulate cardiac tissue; and
   a threshold detector which detects and provides an output indicative of which of the plurality of pulse amplitude/pulse width combinations has the lowest battery charge drain while still obtaining capture of cardiac tissue, the output of the threshold detector being supplied to the control circuitry, the control circuitry causing the stimulation pulse generator to generate stimulation pulses at one of the plurality of pulse amplitude/pulse width combinations which has the same or higher rheobase value and stimulation/pulse energy content as the pulse amplitude/pulse width combination determined by the threshold detector to have the lowest battery charge drain while still obtaining capture of cardiac tissue;
   wherein the stimulation pulse generator generates stimulation pulses at another pulse amplitude/pulse width combination from the memory which is associated with an incrementally higher rheobase value and stimulation pulse energy content to obtain capture with a safety margin.

21. An implantable cardiac stimulation device as defined in claim 20, wherein the incrementally higher rheobase value and stimulation pulse energy content is the next highest rheobase value and stimulation pulse energy content from the memory.

22. An implantable cardiac stimulation device comprising:
   a memory that stores a plurality of pulse amplitude/pulse width combinations which are associated with different rheobase values, each of the combinations having the lowest battery charge drain of any pulse amplitude/pulse width combination having at least the rheobase value of that particular combination;
   a stimulation pulse generator that generates stimulation pulses at a selected pulse amplitude/pulse width combination to stimulate cardiac tissue; and
   a capture detector which detects whether the stimulation pulses obtain capture of cardiac tissue, the capture detector causing the stimulation pulse generator to generate stimulation pulses at the selected pulse amplitude/pulse width combination if the stimulation pulses capture cardiac tissue, the output of the automatic capture detector causing the stimulation pulse generator to generate stimulation pulses at another pulse amplitude/pulse width combination which is associated with an incrementally higher rheobase value from the memory to obtain capture with a safety margin.

23. An implantable cardiac stimulation device comprising:
   means for providing power to the stimulation device;
   means for providing stimulation pulses to cardiac tissue, such stimulation pulses have selectable pulse shapes;
   means for selecting a pulse shape from a plurality of selectable pulse shapes, each pulse being defined by a pulse amplitude and pulse width, forming a unique pair thereby, each pair having associated therewith a specific rheobase value, a pulse shape being selected to provide the lowest battery drain relative to other pairs having the same specific rheobase value; and
   means for detecting whether capture of the cardiac tissue has occurred and for triggering the selection means to select a pair with an incrementally higher rheobase value to obtain capture with a safety margin.

24. An implantable cardiac stimulation device as defined in claim 23, further comprising:
   means for storing the plurality of selectable pulse shapes and their associated specific rheobase value, such plurality including only those pairs that provide the lowest battery drain relative to the other pairs having the same specific rheobase value.

25. An implantable cardiac stimulation device as defined in claim 24, further comprising:

means for sequentially selecting during periods of sustained detected capture, a pair with an incrementally lower rheobase value until capture is lost and selecting immediately thereafter the last pair wherein capture was obtained.

26. An implantable cardiac stimulation device as defined in claim 25, wherein the selecting means maintains cardiac stimulation using the selected last pair only if capture is obtained for at least two consecutive cardiac timing cycles.

27. An implantable cardiac stimulation device as defined in claim 24, wherein the incrementally higher rheobase value is the next highest rheobase value from the means for storing the plurality of selectable pulse shapes.

28. In an implantable cardiac stimulation device, a method of selecting a stimulation energy level for the device, the method comprising:

a) selecting an initial rheobase value to use to stimulate the heart;
b) determining a corresponding pulse amplitude/pulse width combination for the selected rheobase value, where the combination provides relatively low battery charge drain for the rheobase value;
c) determining whether applied pulses at the combination level capture the heart;
d) selecting another rheobase value if the applied pulses fail to capture the heart;
e) repeating actions b) through d) to determine at least one rheobase value that results in capture of the heart; and
f) generating stimulation pulses at a value that is incrementally higher than the rheobase value that results in capture of the heart to obtain capture with a safety margin.

* * * * *